United States Patent
Chen et al.

(10) Patent No.: US 11,324,899 B2
(45) Date of Patent: May 10, 2022

(54) NEBULIZER

(71) Applicant: National Taiwan University, Taipei (TW)

(72) Inventors: Chih-Chieh Chen, Taipei (TW); Sheng-Hsiu Huang, Taipei (TW); Chih-Wei Lin, Taipei (TW); Yu-Mei Kuo, Taipei (TW); Wei-Ren Ke, Taipei (TW)

(73) Assignee: National Taiwan University, Taipei (TW)

( * ) Notice: Subject to any disclaimer, the term of this patent is extended or adjusted under 35 U.S.C. 154(b) by 648 days.

(21) Appl. No.: 16/165,124

(22) Filed: Oct. 19, 2018

(65) Prior Publication Data
US 2019/0374730 A1 Dec. 12, 2019

(30) Foreign Application Priority Data
Jun. 6, 2018 (TW) .......................... TW107119467

(51) Int. Cl.
*A61M 11/00* (2006.01)

(52) U.S. Cl.
CPC .................................. *A61M 11/00* (2013.01)

(58) Field of Classification Search
CPC .... A61M 11/00–02; A61M 11/04–048; A61M 11/06–065; A61M 11/08; A61M 16/00; A61M 16/0003–0012; A61M 16/14–186; A61M 15/00; A61M 15/0086–0098; A61M 15/06; A61M 15/08–085; A61M 15/056; A61M 15/006; A61M 15/0065–0083; A24F 47/00; A24F 47/002; A24F 47/004; A24F 47/008

See application file for complete search history.

(56) References Cited

U.S. PATENT DOCUMENTS

| | | | | |
|---|---|---|---|---|
| 6,014,970 A | * | 1/2000 | Ivri | .................. A61M 15/0085 128/200.14 |
| 2011/0265806 A1 | * | 11/2011 | Alarcon | .................. A24F 40/50 131/273 |
| 2016/0193434 A1 | * | 7/2016 | Gleixner | ........... A61M 15/0066 128/200.16 |

* cited by examiner

*Primary Examiner* — Victoria Murphy
*Assistant Examiner* — Ned T Heffner
(74) *Attorney, Agent, or Firm* — Mintz Levin Cohn Ferris Glovsky and Popeo, P.C.; Peter F. Corless; Joohee Lee (57) ABSTRACT

A nebulizer with orientation independent operation is provided. The nebulizer includes an outer tube, an inner tube provided in the outer tube, and a mesh structure disposed above an end of the outer tube. A first channel, a main channel, and a second channel are formed between the outer tube and the inner tube. When in use, capillary force is created in the main channel, such that a liquid contained in the inner tube can be transported sequentially through the second channel, the main channel, and the first channel to the mesh structure. The liquid is nebulized and dispersed into the air through vibrations of the mesh structure actuated by an annular vibration source.

13 Claims, 6 Drawing Sheets

FIG. 4C

NEBULIZER

CROSS-REFERENCE TO RELATED APPLICATION

This Application claims under 35 U.S.C. § 119(a) the benefit of Taiwanese Patent Application No. 107119467 filed on Jun. 6, 2018. The entire contents of these applications are incorporated herein by reference in their entirety.

BACKGROUND

1. Technical Field

The present disclosure relates to nebulizers, and, more particularly, to a nebulizer with an orientation-independent operation.

2. Description of the Prior Art

Nebulizers currently available may be limited by the orientation for using. For example, when a nebulizer is tilted, aerosol droplets may be prevented from being generated as the solution inside the nebulizer cannot be effectively transported, it might also lead to spillage of the solution. For infants and young children or patients who are sick in bed, the limitation in the spraying direction can cause inconvenience in use.

Some conventional nebulizers use absorbent cotton to produce a capillary force to transport the solution within the container, thereby avoiding being constrained by the spraying direction.

However, the disadvantage of using an absorbent-cotton transfer solution is that a significant quantity of solution would remain in the absorbent cotton due to its high packing density, resulting in a high residual amount of the solution in the nebulizer, and consequently a low amount of nebulization of the solution. This not only wastes the solution, but also may cause a lack of drug dose when used for treatment. In addition, the rate at which the solution is transported often varies owing to the difficulties in controlling the structural and surface properties of the absorbent cottons. In addition, cleaning and maintenance are also an issue if absorbent cotton is used in the nebulizer.

Therefore, there is a need for a solution that addresses the aforementioned shortcomings in the prior art.

SUMMARY

In view of the aforementioned shortcomings of the prior art, the present disclosure provides a nebulizer, which may include: an outer tube including a first wall, a first end formed with an opening, a second end opposing the first end and being closed, and a receiving space formed between the first wall, the first end and the second end; an inner tube disposed in the outer tube and including a first side corresponding to the first end and formed with a first aperture, a second side opposing the first side and formed with a second aperture, and a second wall configured for forming a main channel between the first wall and the second wall, wherein the main channel communicates with the opening, the first aperture and the second aperture; and a mesh structure boned onto the first end and covering the receiving space.

In an embodiment, the outer tube and the inner tube are coaxially disposed.

In an embodiment, the main channel may be between 0.15 and 0.35 mm in width. In another embodiment, the main channel is less than or equal to 0.225 mm in width.

In an embodiment, the first aperture may be less than the second aperture in width. In another embodiment, the first aperture is at least 0.5 mm, preferably 0.8 to 2.0 mm in width.

In an embodiment, the inner tube may further include at least one vent hole formed in the second wall for communicating with the main channel and an inner space of the inner tube.

In an embodiment, the mesh structure includes a plurality of mesh holes.

In an embodiment, the nebulizer may further include an annular vibration source for actuating and vibrating the mesh structure.

As can be seen from the above, when in use, the nebulizer of the present disclosure allows liquid in the inner tube to be transported via the main channel located between the outer tube and the inner tube to the mesh structure by the capillary force created in the main channel, and further allows the liquid to be nebulized and dispersed into the environment by causing vibrations in the mesh structure using the annular vibration source. Thus, compared to the prior art, the nebulizer of the present disclosure can be used in any directions while achieving a desirable amount of aerosol output and a desirable amount of residual liquid in the receiving space.

DETAILED DESCRIPTION OF THE EMBODIMENTS

The technical content of present disclosure is described by the following specific embodiments. One of ordinary skill in the art can readily understand the advantages and effects of the present disclosure upon reading the disclosure of this specification. The present disclosure may also be practiced or applied with other different implementations. Based on different contexts and applications, the various details in this specification can be modified and changed without departing from the spirit of the present disclosure.

It should be noted that the structures, ratios, sizes shown in the drawings appended to this specification are to be construed in conjunction with the disclosure of this specification in order to facilitate understanding of those skilled in the art. They are not meant, in any ways, to limit the implementations of the present disclosure, and therefore have no substantial technical meaning. Without affecting the effects created and objectives achieved by the present disclosure, any modifications, changes or adjustments to the structures, ratio relationships or sizes, are to be construed as fall within the range covered by the technical contents disclosed herein. Meanwhile, terms, such as "first", "second", and the like, are for illustrative purposes only, and are not meant to limit the range implementable by the present disclosure. Any changes or adjustments made to their relative relationships, without modifying the substantial technical contents, are also to be construed as within the range implementable by the present disclosure.

Figure 1:
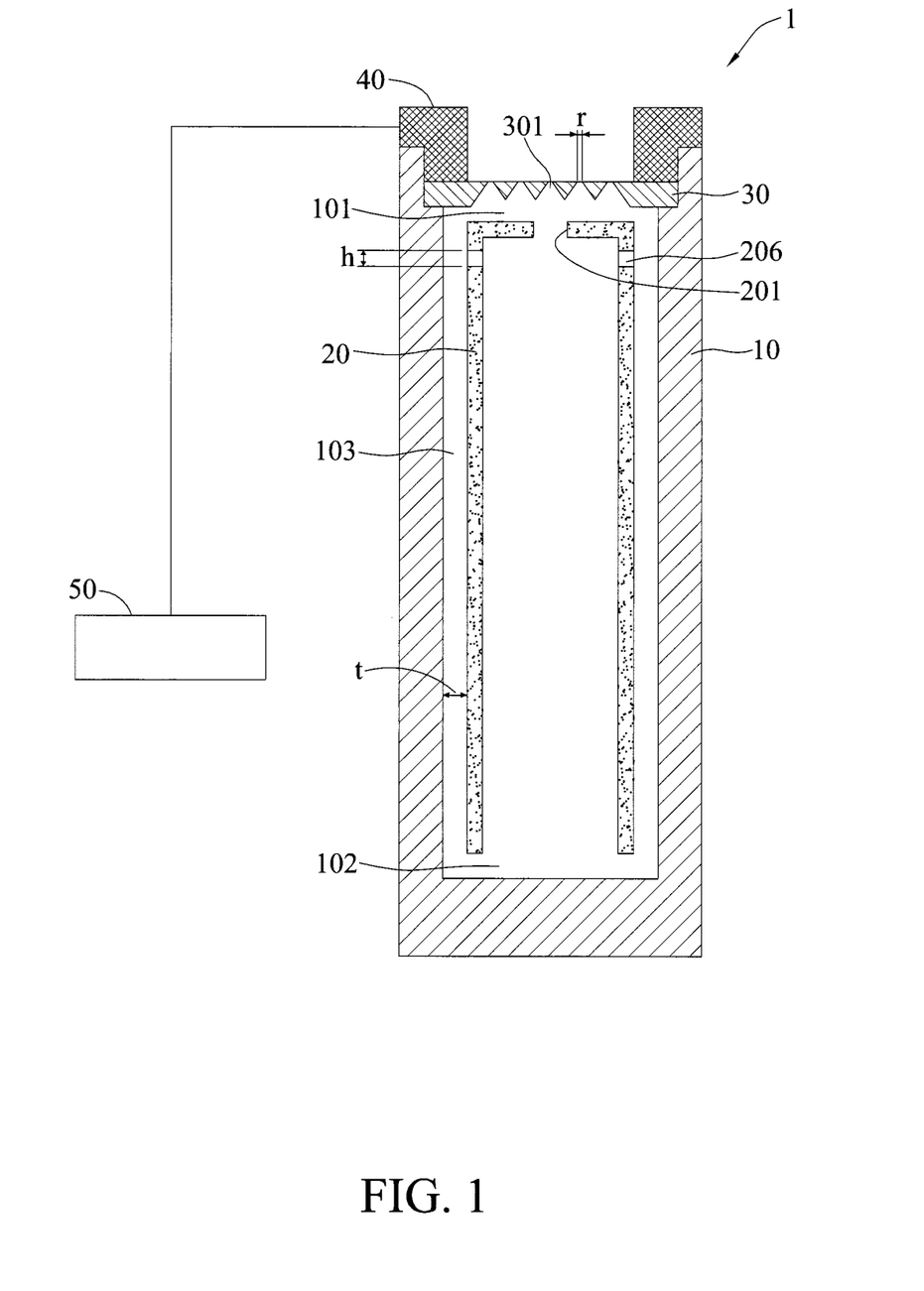
FIG. 1 is a cross-sectional schematic diagram illustrating a nebulizer in accordance with the present disclosure.

FIG. 1 is a cross-sectional schematic diagram illustrating a nebulizer in accordance with the present disclosure. As shown in FIG. 1, a nebulizer 1 includes an outer tube 10, an inner tube 20, a mesh structure 30, an annular vibration source 40, and a drive circuit 50.

Figure 2:
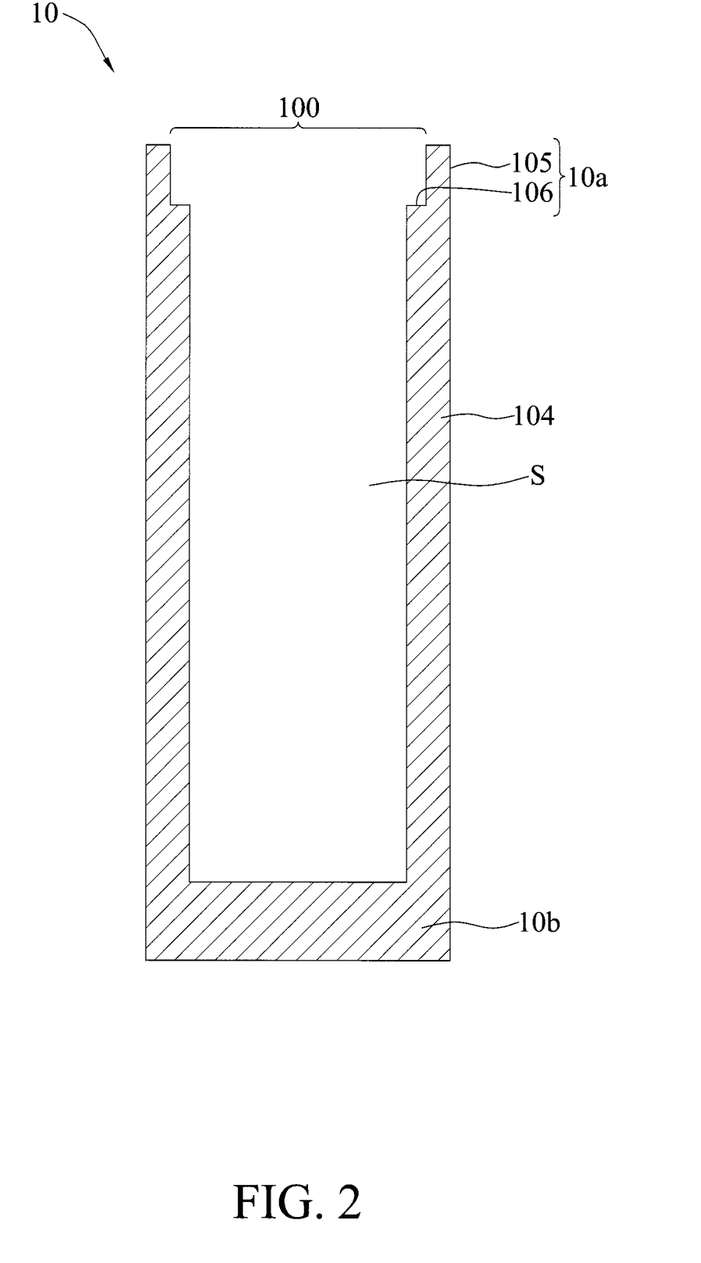
FIG. 2 is a cross-sectional schematic diagram illustrating an outer tube in accordance with the present disclosure.

As shown in FIGS. 1 and 2, the outer tube 10 has a hollow cylindrical shape including a first wall 104, and a first end 10a and a second end 10b adjacent to the two ends of the first wall 104. The first end 10a is adjacent to one end of the first wall 104 and forms an opening 100, while the second end 10b is adjacent to the other end of the first wall 104 and forms a closed end, allowing a receiving space S to be created from the first wall 104 and the second end 10b.

In an embodiment, the first end 10a includes an extension portion 105 extending from an edge of the first wall 104. A step portion 106 is formed between the first wall 104 and the extension portion 105.

Figure 3:
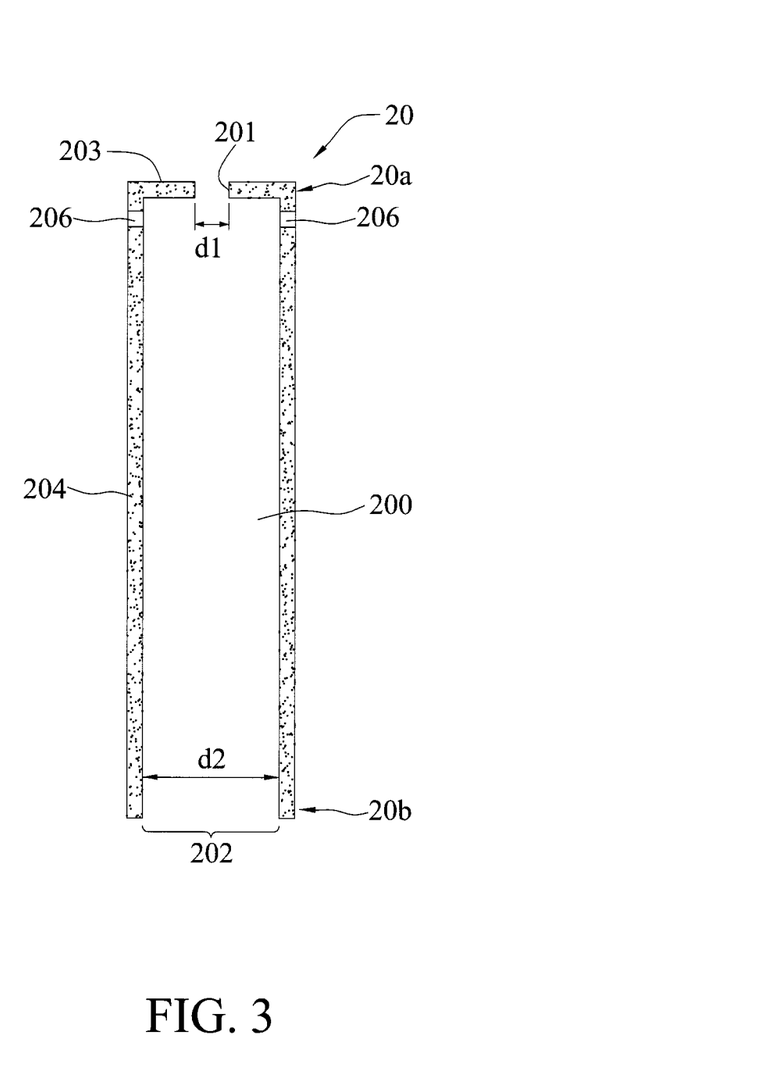
FIG. 3 is a cross-sectional schematic diagram illustrating an inner tube in accordance with the present disclosure.

With reference to FIGS. 1 and 3, the inner tube 20 has a hollow cylindrical shape and is disposed within the receiving space S of the outer tube 10. A main channel 103 is formed between a peripheral wall of the outer tube 10 (i.e., the inner wall face of the first wall 104) and a peripheral wall of the inner tube 20 (i.e., an outer wall face of a second wall 204), wherein the width t of the main channel 103 is, for example, between 0.15 to 0.35 mm; preferably less than or equal to 0.225 mm. In an embodiment, the width t of the main channel 103 may equal to 0.15, 0.175, 0.2, 0.225, 0.25, 0.3 and 0.35 mm.

In an embodiment, the outer tube 10 and the inner tube 20 are coaxially positioned. The inner tube 20 includes the second wall 204 and a cap portion 203 adjacent to the second wall 204. The cap portion 203 is defined as a first side 20a, and a second side 20b is defined as opposite to the first side 20a, wherein the first side 20a corresponds to the first end 10a, such that they are on the same side of the nebulizer 1. A first aperture 201 is formed at the first side 20a (or the cap portion 203), and a second aperture 202 is formed at the second side 20b. In an embodiment, a first channel 101 and a second channel 102 of the same width (or of different widths) extend from the main channel 103. The first channel 101 is in communication with the opening 100 and the first aperture 201 through the first end 10a and the first side 20a, while the second channel 102 is in communication with the second aperture 202 through the second end 10b and the second side 20b.

The second wall 204 and the cap portion 203 define an inner space 200 of the inner tube 20.

The width d1 of the first aperture 201 is less than the width d2 of the second aperture 202. In an embodiment, the first aperture 201 is formed on a portion of cap portion 203 with a width d1 between 0.5 mm and 20 mm, for example, and preferably 1.0 mm. In an embodiment, the width d1 of the first aperture 201 may equal to 0.5, 0.8, 1.0, 1.4 and 2.0 mm. The second side 20b is hollow, thereby forming the second aperture 202.

In an embodiment, the peripheral wall (or the wall 204) of the inner tube 20 is formed with at least one vent hole 206 in communication with the main channel 103 and the inner space 200 of the inner tube 20. In another embodiment, the vent hole 206 is in proximity to the first side 20a and away from the second side 20b. In yet another embodiment, the width h of the vent hole 206 is at least 0.5 mm; preferably between 0.8 and 2.0 mm.

With reference to FIGS. 1 to 3, the mesh structure 30 is provided above the first end 10a of the outer tube 10 to cover the receiving space S shown in FIG. 2.

In an embodiment, the mesh structure 30 sits on the step portion 106 and abuts against the extension portion 105 (i.e., the mesh structure 30 fits tightly with the first end 10a of the outer tube 10), such that the first channel 101 is located between the mesh structure 30 and the first side 20a of the inner tube 20.

In an embodiment, the mesh structure 30 can be made of a metal material, such as stainless steel, but is not limited as such. For example, the mesh structure 30 includes a plurality of mesh holes 301 penetrating the mesh structure 30. In an embodiment, the mesh holes 301 have a conical shape with the larger-hole end facing the first aperture 201 and in communication with the first channel 101 and the smaller-hole end exposed to the external environment. The size r of the smaller-hole end of the mesh hole 301 is, for example, 3 to 10 μm; preferably 6 to 7 μm.

In an embodiment, the mesh structure 30 is a plate-like structure, but is not limited as such.

As shown in FIG. 1, the annular vibration source 40 is coupled to the top of the mesh structure 30, exposing the mesh holes 301 and covering the opening 100 and the extension portion 105.

As shown in FIG. 1, the annular vibration source 40 is used to actuate and vibrate the mesh structure 30.

In an embodiment, the annular vibration source 40 is a piezoelectric element. In another embodiment, the drive circuit 50 is connected with the annular vibration source 40 to provide AC power to the annular vibration source 40 to create a piezoelectric effect. The annular vibration source 40 actuates and vibrates the mesh structure 30.

Figure 4A:
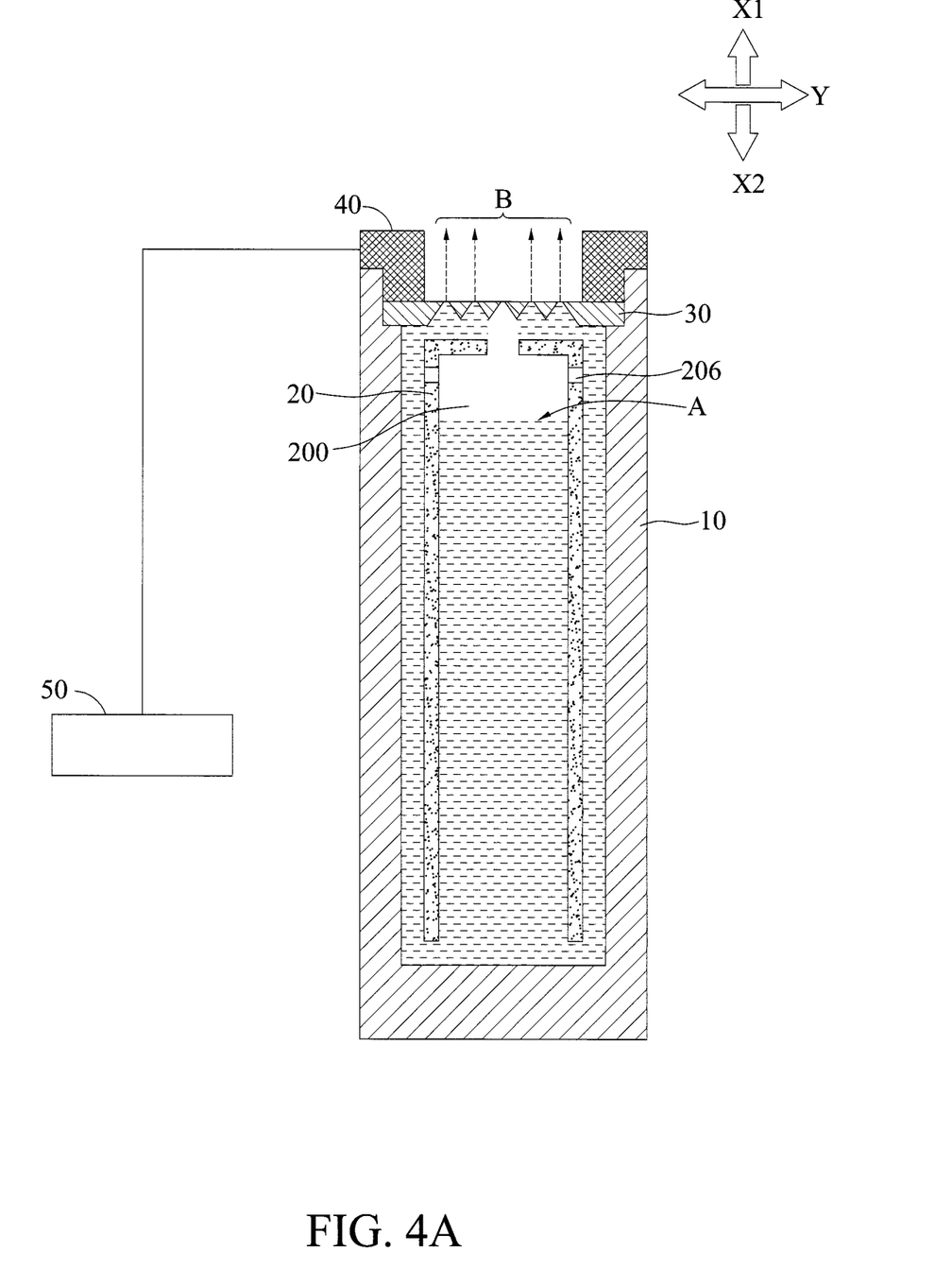
FIGS. 4A to 4C are cross-sectional schematic diagrams illustrating the nebulizer of the present disclosure in use.
Figure 4B:
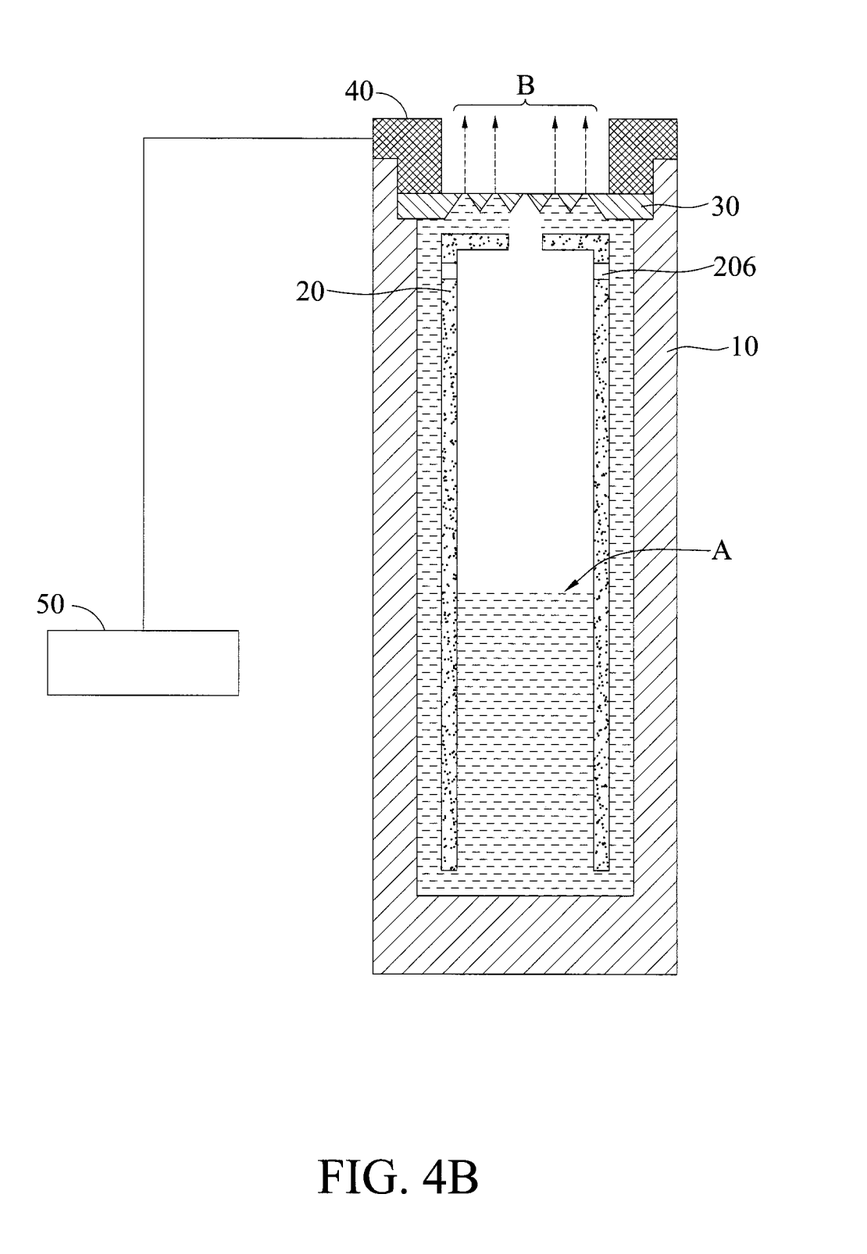
Figure 4C:
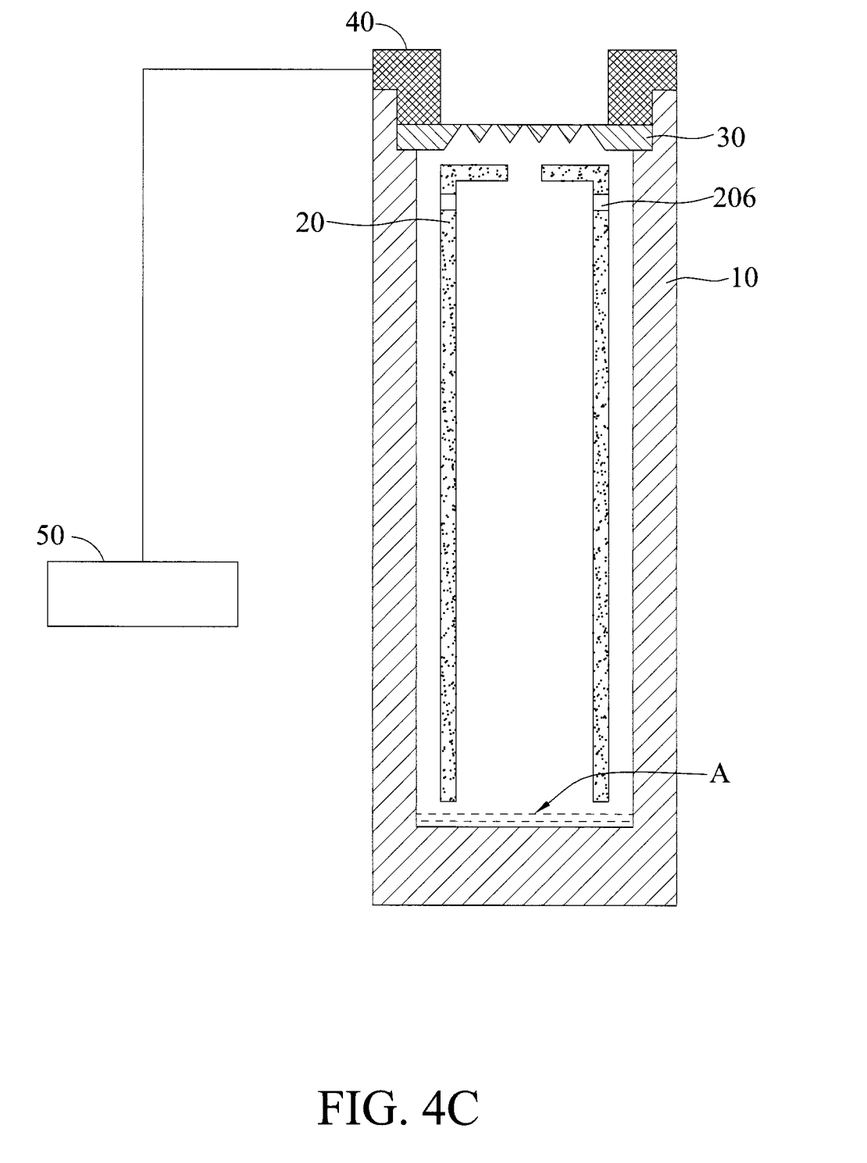

FIGS. 4A to 4C are cross-sectional schematic diagrams illustrating the nebulizer 1 of the present disclosure in use.

As shown in FIG. 4A, the receiving space S of the outer tube 10 or the inner space 200 of the inner tube 20 is filled with a liquid A (about 2 ml), and the height of the liquid A inside the inner space 200 of the inner tube 20 does not exceed the location of the vent hole 206. In an embodiment, the first aperture 201 and the vent hole 206 act as pressure balancing holes. Since capillary forces occur in the main channel 103, the liquid A is transported from the second channel 102 through the main channel 103 to the first channel 101, such that a contact interface is created between the mesh structure 30 and the liquid A in the first channel 101.

As shown in FIG. 4B, by vibrating the mesh structure 30 using the annular vibration source 40, the liquid A at the contact interface is vaporized as mist B, which are then spread into the environment through the mesh holes 301. In an embodiment, after the liquid A at the contact interface is vaporized and spread into the environment, liquid A will be continuously replenished (transported from the second channel 102 to the first channel 101) by the capillary forces created in the main channel 103.

As shown in FIG. 4C, when there is only a very small amount of liquid A left in the receiving space S, the capillary forces created in the main channel 103 can no longer transport the liquid A from the second channel 102 to the first channel 101.

In an embodiment, the width t of the main channel 103 influences the strength of the capillary forces created in the main channel 103, further influences the amount of vaporization of the liquid A and the residual amount of the liquid A in the receiving space S. The width d is thus determined by aiming the nebulizer 1 in three extreme directions.

The first extreme direction is a direction in which the mesh structure 30 is facing upwards, or shown by an arrow direction X1 in FIG. 4A. In an embodiment, when the width t of the main channel 103 was at a minimum width of 0.15 mm, the amount of vapor output from the nebulizer 1 was about 0.1 ml/min, and the residual in the receiving space S was lower than 10%. Then, the width t of the main channel 103 was gradually incremented, and the amount of vapor output also increased accordingly. When the width t of the main channel 103 was at 0.225 mm, the nebulizer 1 experienced the maximum vapor output, and the residual in the receiving space S was lower than 10%.

The second extreme direction is a direction in which the mesh structure 30 is facing sideway, or shown by an arrow direction Y in FIG. 4A. In an embodiment, when the width t of the main channel 103 was between 0.15 and 0.35 mm, the amount of vapor output from the nebulizer 1 was about 0.25 ml/min, and the residual in the receiving space S was lower than 10%.

The third extreme direction is a direction in which the mesh structure 30 is facing downwards, or shown by an arrow direction X2 in FIG. 4A. In an embodiment, when the width t of the main channel 103 was at a minimum width of 0.15 mm, the amount of vapor output from the nebulizer 1 was about 0.21 ml/min, and the residual in the receiving space S was lower than 10%. In an embodiment, the width t of the main channel 103 was gradually incremented, and the amount of vapor output also increased accordingly. The maximum vapor output was 0.40 ml/min, and the residual in the receiving space S was also lower than 10%.

As a result, an optimum value for the width t of the main channel 103 is determined to be 0.225 mm, so as to reduce the differences in the amounts of vapor output at different directions in which the nebulizer 1 is used.

If the width d1 of the first aperture 201 is too small, liquid A tends to form a liquid film at the first aperture 201, which prevents the pressure inside the coaxial tube from being in equilibrium with the external pressure, and the liquid A cannot be transported. Therefore, the width d1 of the first aperture 201 has an influence on how smoothly the liquid A is transported from the second channel 102 to the first channel 101. The width d1 of the first aperture 201 is thus determined by aiming the nebulizer 1 in two extreme directions. Details of which are described below.

The first extreme direction is a direction in which the mesh structure 30 is facing upwards, or shown by the arrow direction X1 in FIG. 4A. In an embodiment, when the width d1 of the first aperture 201 was 0.5 mm, the amount of vapor output from the nebulizer 1 was about 0.1 ml/min, but the residual in the receiving space S reached 90%. Then, the width d1 of first aperture 201 was gradually incremented, and the amount of vapor output also increased accordingly. When the width d1 of the first aperture 201 was at 1-2 mm, the nebulizer 1 experienced the maximum vapor output (approximately 0.25 ml/min).

The second extreme direction is a direction in which the mesh structure 30 is facing downwards, or shown by the arrow direction X2 in FIG. 4A. In an embodiment, when the width d1 of the first aperture 201 was 0.5 mm, the amount of vapor output from the nebulizer 1 was about 0.1 ml/min, but the residual in the receiving space S reached 90%. Then, the width d1 of the first aperture 201 was gradually incremented (e.g., from 0.8 to 2.0 mm), and the amount of vapor output from the nebulizer 1 also increased accordingly to a maximum vapor output of about 0.7 ml/min.

As a result, the width d1 of the first aperture 201 is determined to be between 0.5 and 2.0 mm; preferably 1.0 mm. When the width d1 is 1.0 mm, the amounts of vapor output in the above two extreme direction are high enough with not much difference between them. It should be noted that in the case where the mesh structure 30 of the nebulizer 1 is facing downwards (in the arrow direction X2 shown in FIG. 4A), the first aperture 201 becomes the main transport path of the liquid A.

In conclusion, the nebulizer 1 according to the present disclosure allows the liquid A in the inner tube 20 to be transported via the main channel 103 located between the outer tube 10 and the inner tube 20 to the mesh structure 30 by the capillary forces created in the main channel 103, and further allows the liquid A to be vaporized and dispersed into the environment by causing vibrations in the mesh structure 30 using the annular vibration source 40. Thus, compared to the prior art, the nebulizer 1 of the present disclosure can be used in any orientation while achieving a desirable amount of vapor output and a desirable amount of residual liquid A in the receiving space S (lower than 10% of the original total liquid volume), thereby maximizing the use of the liquid A and satisfying requirements of usage.

The above embodiments are used only to illustrate the principles of the present disclosure and its effect, rather than to limit the present disclosure. The above embodiments can be modified by one of ordinary skill in the art without departing from the spirit and scope of the present disclosure. Therefore, the scope claimed of the present disclosure should be defined by the following claims.

What is claimed is:

1. A nebulizer, comprising:

an outer tube including a first wall, a first end formed with an opening, a second end opposing the first end and being closed, and a receiving space formed between the first wall, the first end and the second end;

an inner tube disposed in the outer tube and including a first side corresponding to the first end and formed with a first aperture, a second side opposing the first side and formed with a second aperture, and a second wall forming a main channel between the first wall and the second wall, wherein a first channel and a second channel extend from the main channel and communicate with each other, wherein the first channel communicates with the opening and the first aperture, wherein the second channel communicates with the second aperture, and wherein the first aperture is located between the first channel and the second channel; an annular vibration source configured for actuating and vibrating the mesh structure; and a mesh structure bonded onto the first end and covering the receiving space, wherein the main channel is between 0.15 mm and 0.35 mm in width, wherein capillary forces occur in the main channel and wherein the nebulizer is configured for use in an arbitrary orientation.

2. The nebulizer of claim 1, wherein the first aperture is less than the second aperture in width.

3. The nebulizer of claim 2, wherein the first aperture is at least 0.5 mm in width.

4. The nebulizer of claim 3, wherein the first aperture is between 0.8 mm and 2.0 mm in width.

5. The nebulizer of claim 1, wherein the inner tube further includes an inner space formed between the second wall, the first aperture and the second aperture.

6. The nebulizer of claim 5, wherein the inner tube further includes at least one vent hole formed in the second wall and communicating with the main channel and the inner space.

7. The nebulizer of claim 5, wherein the inner tube further includes a cap portion formed with the first aperture and adjacent to the second wall.

8. The nebulizer of claim 1, wherein the outer tube further includes an extension portion and a step portion at the first end.

9. The nebulizer of claim 8, wherein the mesh structure is provided on the step portion and abutting against the extension portion.

10. The nebulizer of claim 1, wherein the outer tube and the inner tube are coaxially disposed.

11. The nebulizer of claim 1, wherein the main channel is less than or equal to 0.225 mm in width.

12. The nebulizer of claim 1, wherein the mesh structure includes a plurality of mesh holes.

13. The nebulizer of claim 1, further comprising a driving circuit configured for providing power to the annular vibration source.

* * * * *